(12) United States Patent
Kleyman et al.

(10) Patent No.: US 8,764,645 B2
(45) Date of Patent: Jul. 1, 2014

(54) SURGICAL ACCESS DEVICE AND WOUND PROTECTOR

(71) Applicant: Covidien LP, Mansfield, MA (US)

(72) Inventors: Gennady Kleyman, Brooklyn, NY (US); Gregory Okoniewski, North Haven, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/778,427

(22) Filed: Feb. 27, 2013

(65) Prior Publication Data

US 2013/0253276 A1  Sep. 26, 2013

Related U.S. Application Data

(60) Provisional application No. 61/615,494, filed on Mar. 26, 2012.

(51) Int. Cl.
*A61B 1/32* (2006.01)

(52) U.S. Cl.
USPC .......................................... 600/204; 600/208

(58) Field of Classification Search
USPC ................................................ 600/201–246
See application file for complete search history.

(56) References Cited

U.S. PATENT DOCUMENTS

| | | |
|---|---|---|
| 4,183,357 A | 1/1980 | Bentley et al. |
| 5,366,478 A | 11/1994 | Brinkerhoff et al. |
| 5,524,644 A | 6/1996 | Crook |
| 5,906,577 A | 5/1999 | Beane et al. |
| 5,990,382 A | 11/1999 | Fox |
| 6,033,426 A | 3/2000 | Kaji |
| 6,254,534 B1 | 7/2001 | Butler et al. |
| 6,382,211 B1 | 5/2002 | Crook |
| 6,450,983 B1 | 9/2002 | Rambo |
| 6,589,167 B1 | 7/2003 | Shimomura et al. |
| 6,723,044 B2 | 4/2004 | Pulford et al. |
| 6,846,287 B2 | 1/2005 | Bonadio et al. |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 7,008,377 B2 | 3/2006 | Beane et al. |
| 7,033,319 B2 | 4/2006 | Pulford et al. |
| 7,081,089 B2 | 7/2006 | Bonadio et al. |
| 7,163,510 B2 | 1/2007 | Kahle et al. |
| 7,195,590 B2 | 3/2007 | Butler et al. |
| 7,238,154 B2 | 7/2007 | Ewers et al. |
| 7,344,547 B2 | 3/2008 | Piskun |
| 7,377,898 B2 | 5/2008 | Ewers et al. |
| 7,445,597 B2 | 11/2008 | Butler et al. |
| 7,473,221 B2 | 1/2009 | Ewers et al. |
| 7,540,839 B2 | 6/2009 | Butler et al. |

(Continued)

FOREIGN PATENT DOCUMENTS

| | | |
|---|---|---|
| EP | 0950376 A1 | 10/1999 |
| EP | 2181657 A2 | 5/2010 |

(Continued)

*Primary Examiner* — Mary Hoffman
*Assistant Examiner* — Christina Negrellirodrigue

(57) ABSTRACT

An access device for use in a minimally invasive surgical procedure is disclosed. The access device is configured and adapted to be placed within a body opening to provide access to an underlying body cavity. The access device provides protection to the opening and minimizes contamination and the risk of possible infection.

12 Claims, 4 Drawing Sheets

(56) References Cited

U.S. PATENT DOCUMENTS

| | | |
|---|---|---|
| 7,650,887 B2 | 1/2010 | Nguyen et al. |
| 7,704,207 B2 | 4/2010 | Albrecht et al. |
| 7,727,146 B2 | 6/2010 | Albrecht et al. |
| 8,343,047 B2 | 1/2013 | Albrecht et al. |
| 8,353,824 B2 | 1/2013 | Shelton, IV et al. |
| 2003/0187376 A1 | 10/2003 | Rambo |
| 2004/0092795 A1 | 5/2004 | Bonadio et al. |
| 2005/0020884 A1 | 1/2005 | Hart et al. |
| 2005/0192483 A1 | 9/2005 | Bonadio et al. |
| 2006/0161050 A1 | 7/2006 | Butler et al. |
| 2006/0247498 A1 | 11/2006 | Bonadio et al. |
| 2007/0093695 A1 | 4/2007 | Bonadio et al. |
| 2007/0118122 A1 | 5/2007 | Butler et al. |
| 2007/0118175 A1 | 5/2007 | Butler et al. |
| 2007/0151566 A1 | 7/2007 | Kahle et al. |
| 2007/0203398 A1 | 8/2007 | Bonadio et al. |
| 2007/0208312 A1 | 9/2007 | Norton et al. |
| 2007/0270654 A1 | 11/2007 | Pignato et al. |
| 2008/0021360 A1 | 1/2008 | Fihe et al. |
| 2010/0240960 A1 | 9/2010 | Richard |
| 2010/0286484 A1 | 11/2010 | Stellon et al. |
| 2010/0298646 A1 * | 11/2010 | Stellon et al. .................. 600/208 |
| 2011/0054257 A1 | 3/2011 | Stopek |
| 2011/0125186 A1 | 5/2011 | Fowler et al. |
| 2011/0251464 A1 | 10/2011 | Kleyman |
| 2012/0130177 A1 | 5/2012 | Davis |
| 2012/0130182 A1 | 5/2012 | Rodrigues, Jr. et al. |
| 2012/0157781 A1 | 6/2012 | Kleyman |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |

FOREIGN PATENT DOCUMENTS

| | | |
|---|---|---|
| EP | 2238933 A1 | 10/2010 |
| EP | 2289438 A1 | 3/2011 |
| WO | WO 96/10963 | 4/1996 |
| WO | WO 00/32116 | 6/2000 |
| WO | WO 00/54675 | 9/2000 |
| WO | WO 2004/075741 A2 | 9/2004 |
| WO | WO 2006/110733 A2 | 10/2006 |
| WO | WO 2010/141673 A1 | 12/2010 |

* cited by examiner

SURGICAL ACCESS DEVICE AND WOUND PROTECTOR

CROSS REFERENCE TO RELATED APPLICATION

The present application claims the benefit of and priority to U.S. Provisional Application Ser. No. 61/615,494, filed on Mar. 26, 2012, the entire contents of which are incorporated herein by reference.

BACKGROUND

1. Technical Field

The present disclosure relates to an access device for use in a minimally invasive surgical procedure. In particular, the access device is placed within a tissue tract to provide access to an underlying body cavity while providing protection to the tissue tract.

2. Background of Related Art

During a typical minimally invasive procedure, surgical objects, such as surgical access devices, e.g., trocar and cannula assemblies, or endoscopes, are inserted into the patient's body through an incision or a naturally occurring bodily orifice (e.g., mouth, anus, or vagina) in tissue. To facilitate access to an underlying body cavity, access devices are placed within the within the incision or the naturally occurring bodily orifice. Surgical instruments are placed through the access device.

While it is desirable to minimize the size of an incision or to access internal body structures through a naturally occurring orifice, adequate anatomical exposure is needed to facilitate access to the surgical site. Achieving adequate anatomical exposure can be achieved by separating the walls of the incision or the naturally occurring body orifice. Various retraction devices have been developed to facilitate access to underlying body structures.

As with any surgical procedure, care must be taken to inhibit the possibility of infection that may result if exposed healthy tissue comes in contact with infected or malignant tissue. For example, the spillage of tumor cell clusters may spur the growth of malignant tumors in previously unaffected areas of a patient's body in a process known as tumor seeding. In particular, the sides of a wound a susceptible to infection resulting from contamination. Various wound protection devices have been developed to protect a wound or body orifice during a surgical procedure.

There is a continuing need for new surgical devices that will facilitate access to a surgical site through an incision or naturally occurring bodily orifice while inhibiting contamination of surrounding tissue during the procedure.

SUMMARY

The present disclosure discloses a surgical access device that includes an outer sleeve and one or more inner sleeves that are inwardly disposed of the outer sleeve. The one or more inner sleeves are removable, one at a time, from the surgical access device such that a clean, unused sleeve can be provided without necessitating removal of the surgical access device from the surgical site.

In an embodiment, the surgical access device includes a proximal ring and a distal ring. The outer sleeve is operably coupled to the proximal and distal rings. The proximal and distal rings can function to draw the outer sleeve taut to create a tension in the material of the outer sleeve. This tension may facilitate maintenance of the generally tubular shape of the outer sleeve when the surgical access device is placed within the body opening within the tissue.

The inner sleeves are removably secured to one another and to the outer sleeve. During use, an adhesive layer between the inner sleeves and the outer sleeve can facilitate maintenance of the inner and outer sleeves in a given position relative to one another. A drawstring may be operatively coupled to each of the inner sleeves to facilitate removal of the inner sleeves by proximally translating the drawstring thereby moving the inner sleeve in a corresponding direction.

A method of using the surgical access device is also disclosed. During use, the surgical access device is provided and placed into a body opening. The outer sleeve of the surgical access device facilitates maintaining the body opening in an open state to facilitate access to underlying body structures through the lumen of the surgical access device. As the inner sleeves defining the lumen become contaminated with bodily debris and fluid, the inner sleeves are removed from within the lumen, thereby exposing a previously unexposed inner sleeve and providing the lumen of the surgical access device with a clean surface. Once the desired surgical procedure is completed, the surgical access device is removed from the body opening.

These and other features of the present disclosure will be more fully described with reference to the appended figures.

BRIEF DESCRIPTION OF THE DRAWINGS

By way of description only, embodiments of the present disclosure will be described with reference to the accompanying drawings, in which.

DETAILED DESCRIPTION

Figure 1:
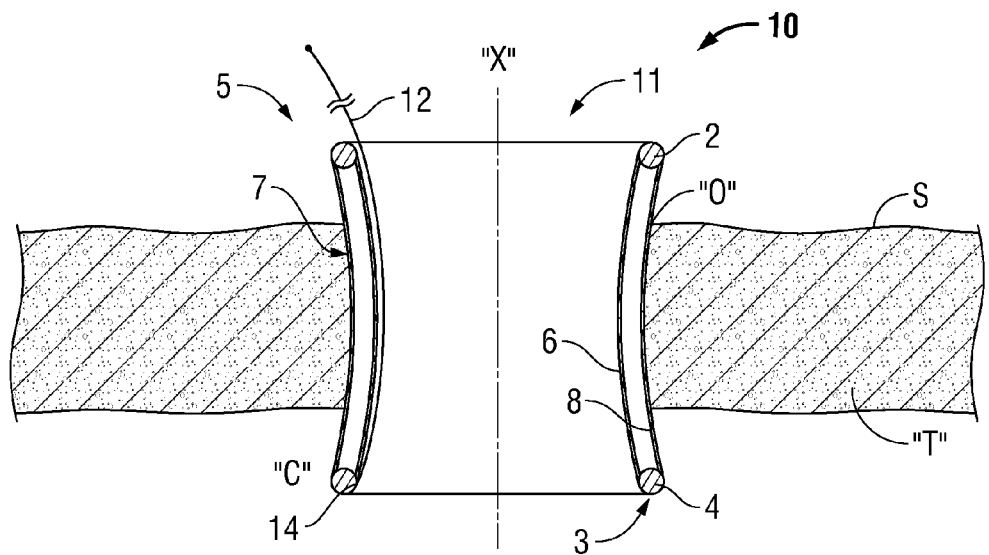
FIG. 1 is a cross-sectional view of a surgical access device in accordance with the present disclosure positioned within a tissue tract and shown in a first condition.

Particular embodiments of the present disclosure will be described herein with reference to the accompanying drawings. In the figures and in the description that follows, in which like reference numerals identify similar or identical elements, the term "proximal" will refer to the end of the apparatus that is closest to the operator during use, while the term "distal" will refer to the end that is farthest from the operator during use.

A first embodiment of a surgical access device will now be described with reference to FIGS. 1 and 2. The surgical access device 10 is configured and adapted to be placed within a body opening "O", e.g., a naturally occurring bodily orifice (e.g., mouth, anus, or vagina) or an incision or wound within a patient's skin "S". The surgical access device 10 is configured and adapted to provide access to underlying body cavity "C" while providing protection to the surfaces of the body opening "O".

The surgical access device 10 includes a trailing or proximal portion 5 and a leading or distal portion 3. The proximal portion 5 of the surgical access device 10 includes a proximal ring 2. The distal portion 3 of the surgical device 10 includes a distal ring 4. An intermediate section 7 is positioned between the proximal portion 5 and the distal portion 3. As shown in FIGS. 1 and 2, the intermediate section 7 includes an outer sleeve 8 and one or more inner sleeves 6. The intermediate section 7 defines a lumen 11 longitudinally extending along longitudinal axis "X".

The outer sleeve 8 is fixed to the proximal ring 2 and the distal ring 4. The outer sleeve 8 may be formed from a length of flexible material that is drawn taut by spacing the proximal ring 2 apart from the distal ring 4 along longitudinal axis "X". In embodiments, the outer sleeve 8 may be formed from a rigid, semi-rigid, or compressible material to facilitate anchoring of the seal anchor member 10 within the body opening "O".

Disposed within and removably coupled to the outer sleeve 8 are one or more inner sleeves 6. The one or more sleeves 6 are positioned between and are removably coupled to the proximal and distal rings 2, 4. The one or more sleeves 6 may each be removably coupled to the proximal ring 2 at fixation point 16 and to the distal ring 4 at fixation point 14. The one or more inner sleeves 6 may be formed from a flexible material that is drawn taut by the proximal and distal ring 2, 4. Each inner sleeve 6 may be removably coupled to fixation points 14, 16 by an adhesive. When drawn taut, the one or more inner sleeves 6 are tensioned and will resist deformation, thereby maintaining a generally cylindrical shape.

Figure 3:
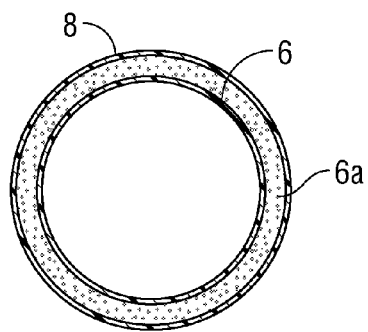
FIG. 3 is a top view of an embodiment of a surgical access device in accordance with the present disclosure.

In an embodiment, as shown in FIG. 3, the inner sleeves 6 and the outer sleeve 8 may form a single structure. Microperforations 6a between each inner sleeve 6 and the outer sleeve 8 facilitate separation of individual inner sleeves 6 from each other and the outer sleeve 8 upon the application of a force F upon an inner sleeve 6.

Figure 2:
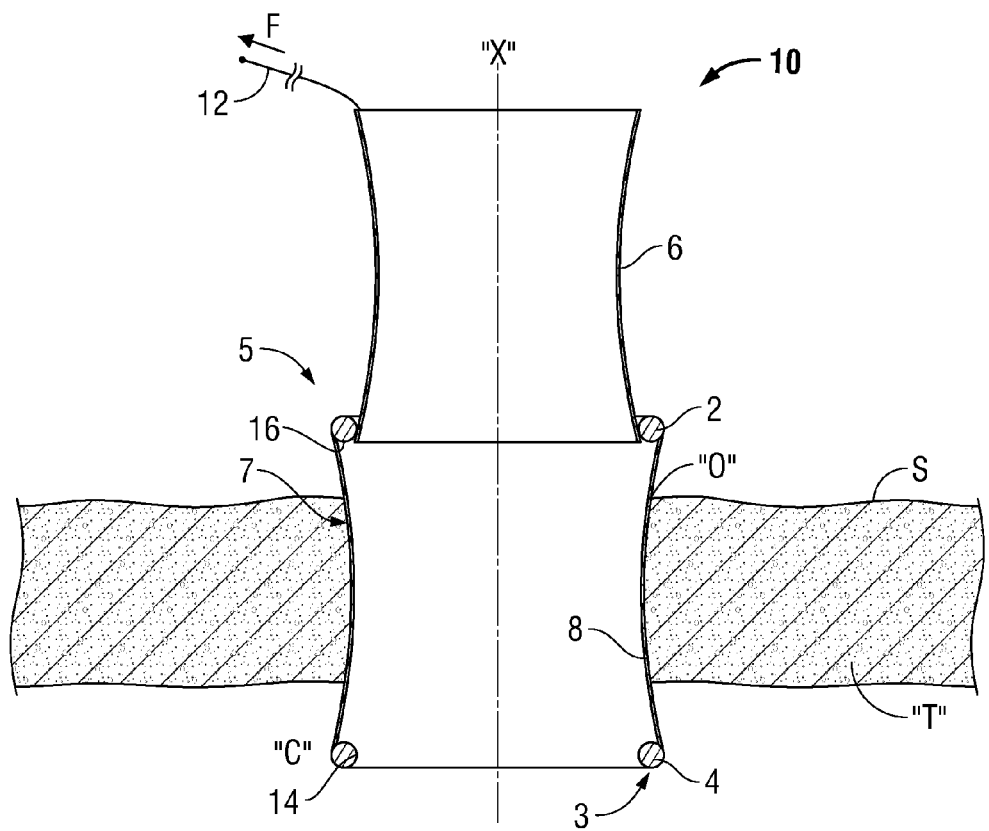
FIG. 2 is a cross-sectional view of the surgical access device of FIG. 1 shown in a second condition.

As shown in FIGS. 1 and 2, a drawstring 12 may be secured to a distal end of each inner sleeve 6. Upon application of force F to the inner sleeve 6 (FIG. 2) in the proximal direction, the inner sleeve 6 separates from the fixation point 14. Continued application of force F to the inner sleeve 6 results in separation of the inner sleeve 6 from fixation point 16 and the removal of the inner sleeve 6 from the lumen 11.

Another embodiment of a surgical access device will now be described with reference to FIGS. 4A and 4B. A surgical access device 20 includes a series of tubular structures 21, 22, 23 that are frictionally engaged with one another. The tubular structures 21, 22, 23 may be formed from a rigid or semi-rigid material to resist the biasing force of the body opening O to maintain the tubular shape of the tubular structures 21, 22, 23. Although shown as including three tubular structures 21, 22, 23, the surgical access device 20 may include a greater or lesser number of such tubular structures. The outermost tubular structure 21 forms an intermediate section 28 that interacts with the walls of the body opening O. An hour-glass configuration of the intermediate section 28 may facilitate securement of the surgical access device 20 within the body opening O. The proximal and distal ends 27, 29 of the surgical access device 20 may be flanged to facilitate securing of the surgical access device 20 within the body opening O.

Figures 4A, 4B:
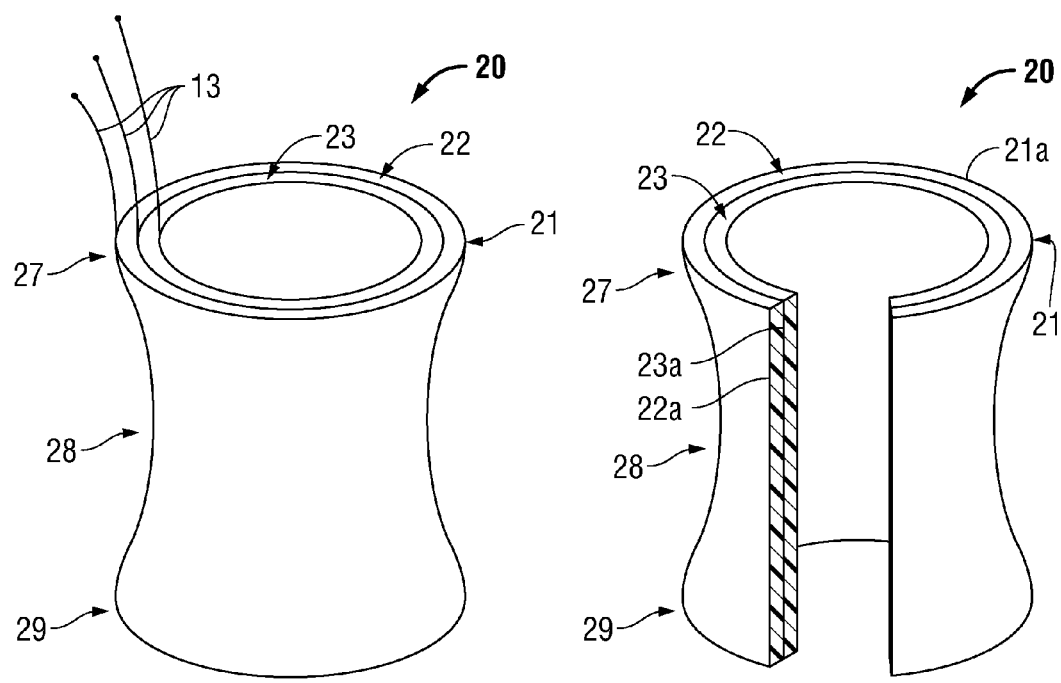
FIG. 4A is a perspective view of an embodiment of a surgical access device in accordance with the present disclosure and shown in a first condition.
FIG. 4B is a partially cutaway view of the surgical access device of FIG. 4A.
Figure 5A:
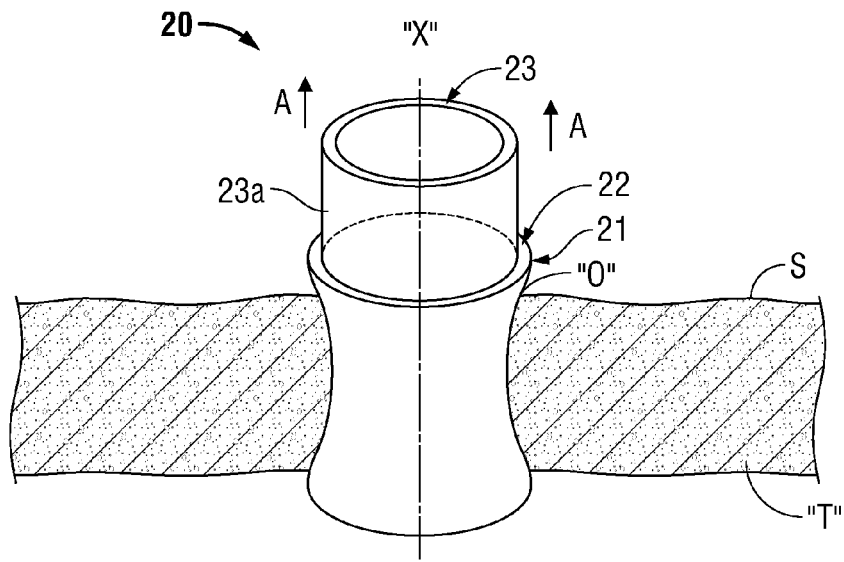
FIG. 5A is a perspective view of the surgical access device of FIG. 4A shown relative to tissue and in an intermediate condition.
Figure 5B:
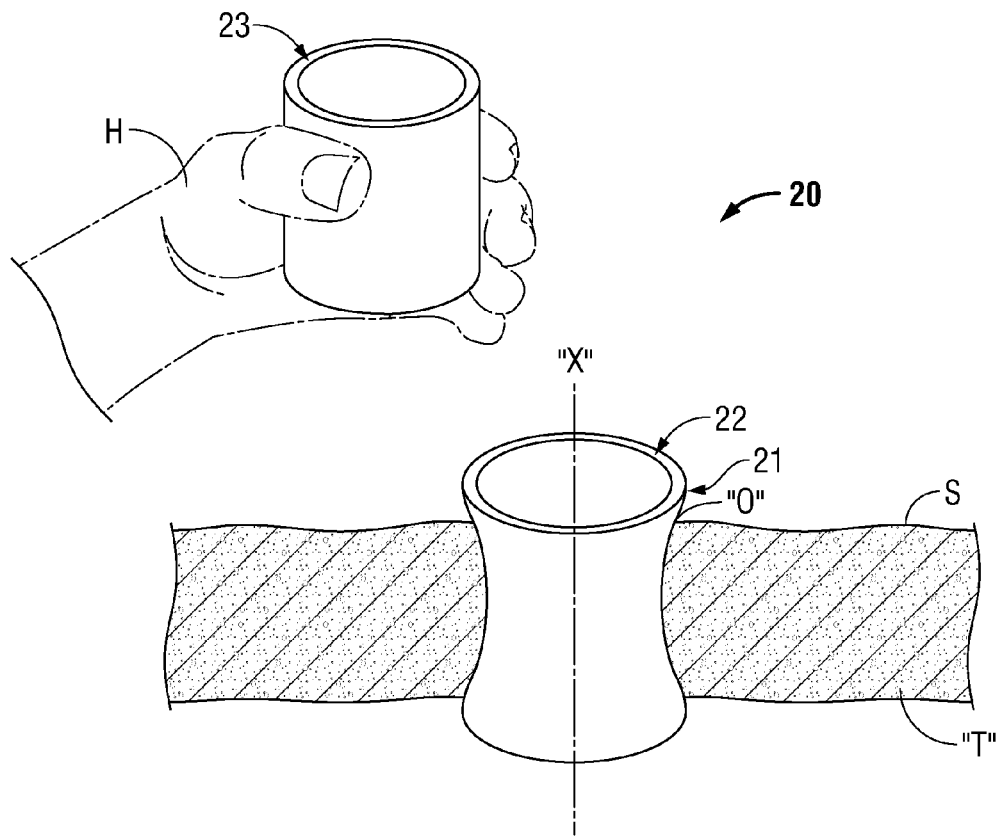
FIG. 5B is the surgical access device as shown in FIG. 5A in a second condition; is a front view of a surgical access device in accordance with the present disclosure.

As shown best in FIG. 4B, the surfaces 21a, 22a, 23a of the tubular structures 22, 23 may include an adhesive layer to inhibit movement of the tubular structures with respect to one another. A drawstring 13 may be coupled to the tubular structures 21, 22, 23 to facilitate removal of each tubular structure 22, 23 from the surgical access device 20. When one of the tubular structures 21, 22, 23 (i.e., the structure having an exposed surface) becomes contaminated, the tubular structure can be removed while maintaining the surgical access device 20 within the body opening O. As shown in FIGS. 5A and 5B, a surgeon H may proximally translate tubular structure 23 in the direction indicated by arrows A, thereby leaving behind the remaining unused tubular structures 21, 22.

Figure 6A:
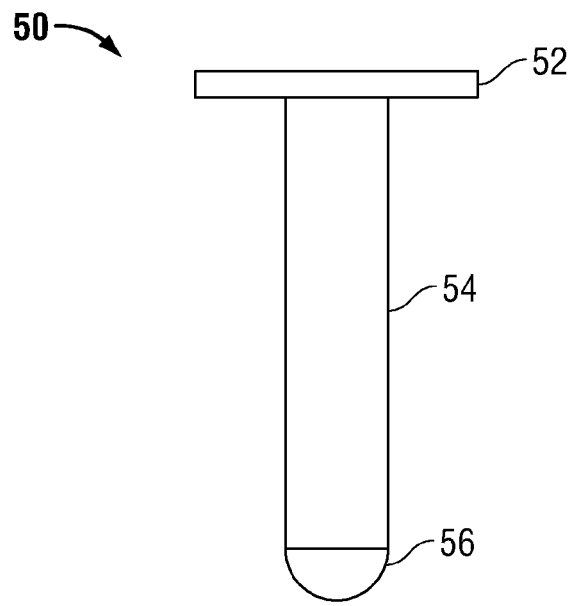
FIG. 6A is a front view of an introducer device.
Figure 6B:
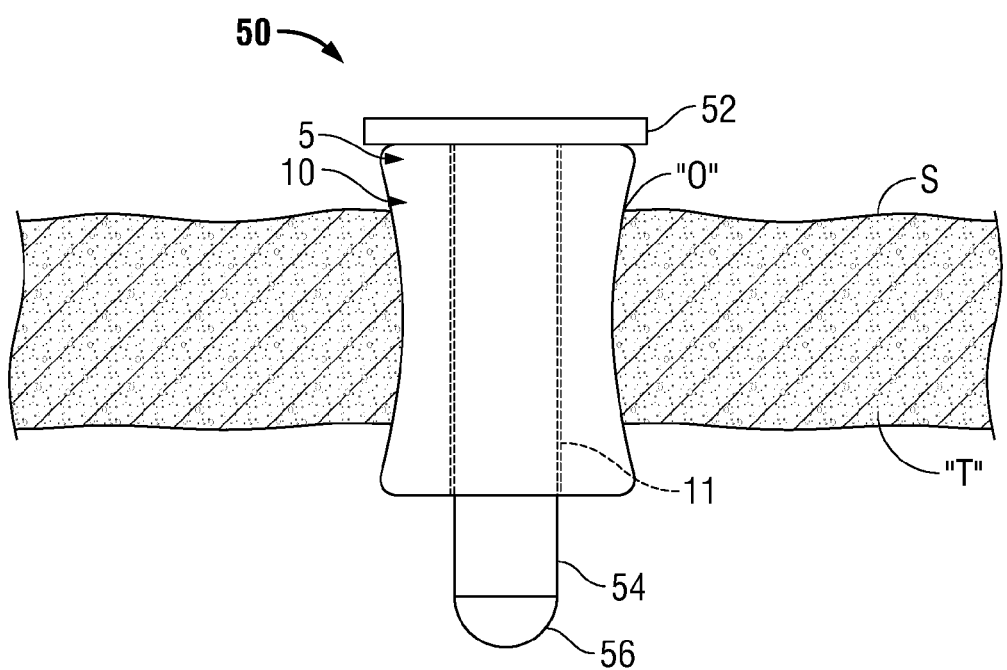
FIG. 6B is a front view of the introducer device of FIG. 6A shown placed within the surgical access device of FIG. 1.

An introducer device 50 may be used to facilitate placement of the surgical access device 10. As shown in FIG. 6A, the introducer device 50 includes a tapered distal end 56, and elongated tubular structure 54, and a flanged proximal end 52. As shown in FIG. 6B, the introducer device is configured and adapted to be placed within the lumen 11 of the surgical access device 10, and the proximal end 52 of the introducer device 50 is configured and adapted to engage the proximal end 5 of the surgical access device 10 such that distal translation of the introducer device 50 pushes the surgical access device into the body opening O of tissue T. In addition, the tapered distal end 56 of the introducer device 50 facilitates placement of the introducer device 50 into the lumen 11 of the surgical access device. Furthermore, the tapered distal end 56 of the introducer device 50 may facilitate the creation or enlargement of the body opening O within the skin S of tissue T.

A method of using the surgical access devices described herein will now be discussed with respect to surgical access device 10. First, introducer 50 may be placed within lumen 11 of the surgical access device 10. The surgical access device 10 is then placed into the body opening O of tissue T by inserting the introducer 50 along with the surgical access device 10 into the body opening O. The tapered distal end 56 facilitates insertion of the surgical access device 10 and helps stretch the body opening O to accommodate reception of the surgical access device 10. The surgical access device 10 is then anchored within the body opening O. The shape, e.g., an hour-glass configuration, of the surgical access device 10 facilitates the anchoring of the surgical access device 10 within the body opening O.

Once the surgical access device 10 is placed within the body opening O, the desired surgical procedure is performed. During the course of the surgery, it may be advantageous to remove inner sleeves 6 as they become contaminated to facilitate maintaining a clean working environment. Removal of the inner sleeves 6 is accomplished by translating each inner sleeve 6 proximally out from the lumen 11. Applying force F in a proximal direction to the drawstring 12 results in separation of the inner sleeve 6 from the surgical access device, and the exposure of the surface of the next remaining inner sleeve 6 or the inner surface of the outer sleeve 8. Once the desired surgical procedure is completed, the surgical access device 10 is removed from the body opening O.

It will be understood by those skilled in the art that various modifications and changes in form and detail may be made to the present disclosure without departing from the scope and spirit of the same. Therefore, the above description should not be construed as limiting, but merely as exemplifications of particular embodiments. While several embodiments of the disclosure have been shown in the drawings, it is not intended that the disclosure be limited thereto. Rather, the disclosure is intended to be read as broadly in scope as the art will allow.

What is claimed is:

1. A surgical access device, comprising:
   a proximal portion;

a distal portion;

an intermediate portion disposed between the proximal and distal portions, the intermediate portion including:

an outer sleeve defining a generally tubular shape and having a first longitudinal dimension; and one or more inner sleeves having a second longitudinal dimension, the first longitudinal dimension of the outer sleeve substantially the same as the second longitudinal dimension of the one or more inner sleeves, the one or more inner sleeves inwardly disposed relative to and removably secured to the outer sleeve, the one or more inner sleeves defining a longitudinally extending lumen; and a drawstring coupled to a distal end of the one or more inner sleeves, wherein application of a force to the drawstring facilitates removal of the one or more inner sleeves from the surgical access device.

2. A surgical access device of claim 1, wherein the outer sleeve and the one or more inner sleeves are integral and separable.

3. The surgical access device of claim 1, further comprising:

a proximal ring coupled to a proximal end of the outer sleeve; and a distal ring coupled to a distal end of the outer sleeve.

4. The surgical access device of claim 1, wherein an adhesive releasably couples the one or more inner sleeves to each other.

5. The surgical access device of claim 1, wherein the one or more inner sleeves are frictionally secured within the surgical access device.

6. The surgical access device of claim 1, wherein the outer sleeve and the one or more inner sleeves include micro-perforations.

7. A method of performing surgery comprising:

providing a surgical access device including:

a proximal portion;

a distal portion; and an intermediate portion disposed between the proximal and distal portions, the intermediate portion including:

an outer sleeve defining a tubular shape; and one or more inner sleeves inwardly disposed relative and removably secured to the outer sleeve, the one or more inner sleeves defining a longitudinally extending lumen, the one or more inner sleeves selectively removable from the surgical access device;

placing the surgical access device into a body opening to access an underlying body cavity;

performing a surgical procedure;

removing at least one of the one or more sleeves during the course of the surgical procedure by applying a force to a drawstring coupled to a distal end of the at least one of the one or more inner sleeves; and removing the surgical access device from the body opening.

8. A surgical access device, comprising:

a proximal portion;

a distal portion; and an intermediate portion disposed between the proximal and distal portions, the intermediate portion including:

an outer sleeve defining a generally tubular shape and having a first longitudinal dimension; and one or more inner sleeves having a second longitudinal dimension, the first longitudinal dimension of the outer sleeve substantially the same as the second longitudinal dimension of the one or more inner sleeves, the one or more inner sleeves inwardly disposed relative to and removably secured to the outer sleeve, the one or more inner sleeves defining a longitudinally extending lumen, wherein the outer sleeve and the one or more inner sleeves include micro-perforations.

9. A surgical access device of claim 8, wherein the outer sleeve and the one or more inner sleeves are integral and separable.

10. The surgical access device of claim 8, further including:

a proximal ring coupled to a proximal end of the outer sleeve; and a distal ring coupled to a distal end of the outer sleeve.

11. The surgical access device of claim 8, wherein an adhesive releasably couples the one or more inner sleeves to each other.

12. The surgical access device of claim 8, wherein the one or more inner sleeves are frictionally secured within the surgical access device.

* * * * *